(12) United States Patent
Klein et al.

(10) Patent No.: US 9,011,485 B2
(45) Date of Patent: Apr. 21, 2015

(54) IMPLANTABLE BIODEGRADABLE WOUND CLOSURE DEVICE AND METHOD

(75) Inventors: Michael Sigmund Klein, Salinas, CA (US); Charles Eichorn Witherell, Salinas, CA (US)

(73) Assignee: Lapiq, Inc, Los Altos, CA (US)

( * ) Notice: Subject to any disclaimer, the term of this patent is extended or adjusted under 35 U.S.C. 154(b) by 404 days.

(21) Appl. No.: 13/475,996

(22) Filed: May 20, 2012

(65) Prior Publication Data

US 2013/0012987 A1 Jan. 10, 2013

Related U.S. Application Data

(63) Continuation-in-part of application No. 12/758,027, filed on Apr. 11, 2010, now Pat. No. 8,506,593.

(51) Int. Cl.
*A61B 17/08* (2006.01)
*A61B 17/00* (2006.01)

(52) U.S. Cl.
CPC ... *A61B 17/0057* (2013.01); *A61B 2017/00637* (2013.01); *A61B 2017/00646* (2013.01)

(58) Field of Classification Search
USPC .......... 606/153, 154, 157, 158, 213, 215, 606/301–310, 313, 314, 319, 320, 322, 323, 606/326, 327, 328; 24/94–96, 105, 289, 24/290, 453, 458, 581.11; 623/23.72
See application file for complete search history.

(56) References Cited

U.S. PATENT DOCUMENTS

| | | | | |
|---|---|---|---|---|
| 570,872 | A * | 11/1896 | Gardner | 24/105 |
| 1,026,017 | A * | 5/1912 | Anderson | 24/114.8 |
| 1,233,455 | A * | 7/1917 | Doucette | 24/105 |
| 3,494,246 | A * | 2/1970 | Hensley | 411/362 |
| 5,366,460 | A | 11/1994 | Eberbach | |
| 6,120,539 | A | 9/2000 | Eldridge | |
| 6,241,768 | B1 | 6/2001 | Agarwal | |
| 7,189,024 | B2 * | 3/2007 | Cameron | 403/306 |
| 7,788,772 | B2 * | 9/2010 | Dandurand | 24/105 |
| 8,096,023 | B2 * | 1/2012 | Orza | 24/104 |
| 2003/0181988 | A1 | 9/2003 | Rousseau | |
| 2006/0015142 | A1 | 1/2006 | Malazgirt | |
| 2006/0282105 | A1 | 12/2006 | Ford | |
| 2010/0145364 | A1 | 6/2010 | Keren | |
| 2012/0016385 | A1 | 1/2012 | Keren | |

OTHER PUBLICATIONS

Maurus, P.B. and Kaeding, C.C., "Bioabsorbable Implant Material Review", Oper. Tech. Sports Med 12, 158-160, 2004.

(Continued)

*Primary Examiner* — Thomas McEvoy
(74) *Attorney, Agent, or Firm* — Michael Toback (57) ABSTRACT

An implantable biodegradable device consisting of an inner button attached to a cylindrical segment, and an outer button attached to a retainment feature. The cylindrical segment is threaded on one end, with a surface groove. The retainment feature consists of radial strips with bent ends. The diameter of the radial strips is slightly larger than the outer diameter of the cylinder. The bent ends fit into the groove. An insertion tool can attach to the threads in the cylinder and push the inner button through a wound, then, holding the inner button in place, push the outer button toward the inner button until the bent ends engage with the groove. The top of the threaded end of the cylindrical segment is adjacent to the back surface of the outer button when the bent ends of the retainment feature are engaged with the groove.

12 Claims, 10 Drawing Sheets

(56) References Cited

OTHER PUBLICATIONS

Middleton, J. and Tipton A. "Synthetic Biodegradable Polymers As Medical Devices" Medical Plastics and Biomaterials Magazine, Mar. 1998.

Gilding, D.K. and Reed, A.M. "Biodegradable Polymers for Use in Surgery," Polymer, 20, 1459-1464 (Dec. 1979).

("Plastic That Comes Alive: Biodegradable plastic scaffolds support living cells in three dimensional matrices so they can grow together into tissues and even whole organs" by Cat Faber Strange Horizons http://www.strangehorizons.com/2001/20010305/plastic.shtml.

Astete, C.E. and Sabliov, C.M., "Synthesis and Characterization of PLGA Nanoparticles", Journal of Biomaterials Science Polymer Edition 17 (3) 247-289 (2006).

* cited by examiner

IMPLANTABLE BIODEGRADABLE WOUND CLOSURE DEVICE AND METHOD

This application is a continuation in part of application Ser. No. 12/758,027 filed on Apr. 11, 2010, titled "An Implantable Biodegradable Wound Closure Device and Method".

The present invention generally relates to a wound closure device and a method that is used to repair the defect typically left in the fascia layer after laparoscopic surgery by an instrument called a trocar.

BACKGROUND OF THE INVENTION

Field of the Invention

Laparoscopic surgery was introduced as an alternative to open surgical methods. Also referred to as minimally invasive surgery, the technique allows for small incision access to the intra-abdominal cavity. The approach utilizes specialized equipment for the purposes of inflating the abdominal cavity with gas, deploying and exchanging instruments during the operation, and real time imaging with a videoscopic camera.

A laparoscopic trocar is a surgical device used for laparoscopic procedures to pierce and access the wall of an anatomical cavity, thereby forming a passageway providing communication with the inside of the cavity. Other medical instruments such as videoscopes and operating instruments can thereafter be inserted through the passageway to perform various surgical procedures within the anatomical cavity.

When the procedures are over, the laparoscopic trocar is removed, leaving a residual defect in the fascia-peritoneal layer. Laparoscopic trocars are typically 5-15 mm in diameter. Any port size larger than 5 mm should be closed because of the risk of hernias. The defect is located deep in the abdominal wall, making it difficult to repair.

The wound shape varies depending on the trocar profile. In some cases, the fascia layer defect is just a single slit in profile, while others are more star shaped. The tissue flaps from trocar wounds need to be held together mechanically during the early stages of healing.

Within 48 hours, the regeneration of peritoneum and local inflammation form a structural matrix strong enough to hold the wound edges together. By using a compressive mechanism to hold the tissue in place, healing is supported even if the compressive mechanism does not cover the entire wound.

Conventional suturing of a trocar site fascial defect is often technically difficult, frustrating, and incomplete due to the limited size of skin incision, the depth of the subcutaneous fatty layer, and need for blind manipulation of tissue at the anatomically important fascial level. Moreover, suturing that involves placement of deep sutures after the abdomen has been decompressed is a potentially dangerous maneuver that surgeons would prefer to avoid.

Trocar site herniation is a recognized complication of laparoscopic surgery. Omental and sometimes intestinal herniation with incarceration and obstruction has been documented in recent surgical literature. This occurs at trocar insertion sites that were incompletely repaired at operation.

The need to perform fascial closure of any trocar insertion site 10 mm or larger has now been established and is routinely practiced worldwide. However, the repair of 5 mm sized defects in obese patients is prudent because high pressure tension stresses within the abdominal wall increase the risk of hernia.

Conventional suturing of a trocar site fascial defect is often technically difficult, frustrating, indefinitely successful, and even sometimes dangerous due to the limited size of skin incision, the depth of the subcutaneous fatty layer, and necessity of blind manipulation. Moreover, the suturing that involves placement of deep blind sutures after the abdomen has been decompressed is a dangerous manipulation that surgeons tend to avoid.

Reliable closure of the residual trocar defect in overweight and obese patients is very difficult to achieve. An overall 6% hernia complication rate has been reported. The economic impact is attributed to need for reoperation, re-hospitalization, and extended disability.

A number of techniques and instruments have been devised to facilitate a safe and secure closure of the fascial defect. These are all based on the concept of a single suture closure method or technique. A variety of modified straight needles with grasping features are used for this purpose, including the Carter-Thomason or Riza-Ribe® products. Although described as quick and easy methods, these techniques require insertion under direct visualization to prevent injury to bowel or other structures within the abdominal cavity.

Repeated insertion of needle suture graspers is required to repair multiple trocar defects, thereby increasing the overall risk of iatrogenic injury. This technique is clumsy, awkward, and time consuming. As a closure method based on the application of "single" suture, it is limited in terms of furthering overall wound healing goals.

As surgical manipulation of the wound increases, trauma, inflammation, and risk of ensuing infection rise considerably. Edema, seroma and/or hematoma formation around the wound combine to further increase the risk of dehiscence and hernia formation.

Excessive traumatic manipulation and suturing with heavy sutures undermine the "minimally invasive" advantages of laparoscopic surgery. In the post-operative period, patients are subject to risk of pain and hernia complications at their trocar sites. The problems associated with trocar wound hernia are troubling to the patient as these develop after discharge on the first or second postoperative day. The problems of the wound would cause the patient to refer back to the institution.

Any of these suturing techniques are to be done under direct vision. It is however impossible to repair the last trocar wound under direct vision. Unless a 5 mm scope is used, the last large trocar site can only be blindly closed with conventional sutures.

No matter which suturing technique or needle is used, it has not been possible to completely eliminate the formation of trocar site hernias. As complex laparoscopic surgery becomes more common, the incidence of this complication is expected to increase beyond the current reported rate of 3-6%. The persistently high rates of trocar hernia complications show that there is a need for more reliable trocar closure methods.

Eldridge and Titone (U.S. Pat. No. 6,120,539 Issued Sep. 19, 2000) proposed a prosthetic repair fabric constructed from a combination of non-absorbable tissue-infiltratable fabric which faces the anterior surface of the fascia and an adhesion-resistant barrier which faces outward from the fascia. This prosthetic requires the use of sutures to hold it in place.

Eberbach (U.S. Pat. No. 5,366,460 Issued Nov. 22, 1994) proposed the use of a non-biodegradable fabric-coated loop inserted through the defect into the fascia wall, pressing against the posterior fascia wall from the intra-abdominal pressure.

Agarwal et al (U.S. Pat. No. 6,241,768 Issued Jun. 5, 2001) proposed a prosthetic device made of a biocompatible non-biodegradable mesh, which sits across the fascia defect using the abdominal pressure to hold it in place.

Rousseau (Pat Pub #20030181988) proposed a plug made of biocompatible non-biodegradable material which covers the anterior side of the fascia, the defect, as well as the posterior side of the fascia.

Malazgirt (Pat Pub #20060015142) proposed a plug/mesh non-biodegradable combination for repair of large trocar wounds. It is stated that it requires at least a "clean flat area around with a radius of 2.5 cm", and requires staples to hold it in place.

Ford and Torres (Pat Pub #20060282105) proposed a patch with a tether or strap, all made of non-biodegradable biocompatible material placed against the anterior wall of the fascia defect.

Keren and Lore (Pat Pub #20100145364 and 20120016385) is an automated suture port closure device enables port closure with no exposed needle. It uses a system of needle guides and multiple needles which are activated by the surgeon once the device is inside the port.

A prior invention of the inventors (Pat Pub #20110251638) compressed tissue laterally between two biodegradable buttons.

SUMMARY

An implantable biodegradable device to promote the healing of a wound consisting of an inner button attached to a cylindrical segment, and an outer button attached to a spring retainment feature. The cylindrical segment is threaded at the opposing end, with a groove on its surface. The spring retainment feature consists of radial strips with bent ends, where the diameter of the radial strips is slightly larger than the outer diameter of the cylinder, and the bent ends fit into the groove. An insertion tool can attach to the threads in the cylinder and push the inner button through the wound, then holding the inner button in place, push the outer button toward the inner button until the bent ends engage with the groove, finally detaching the insertion tool from the threads. The device is constructed so that the top of the threaded end of the cylindrical segment is adjacent to the back surface of the outer button when the bent ends of the spring retainment feature are engaged with the groove.

DESCRIPTION OF THE PREFERRED EMBODIMENT

Figure 1:
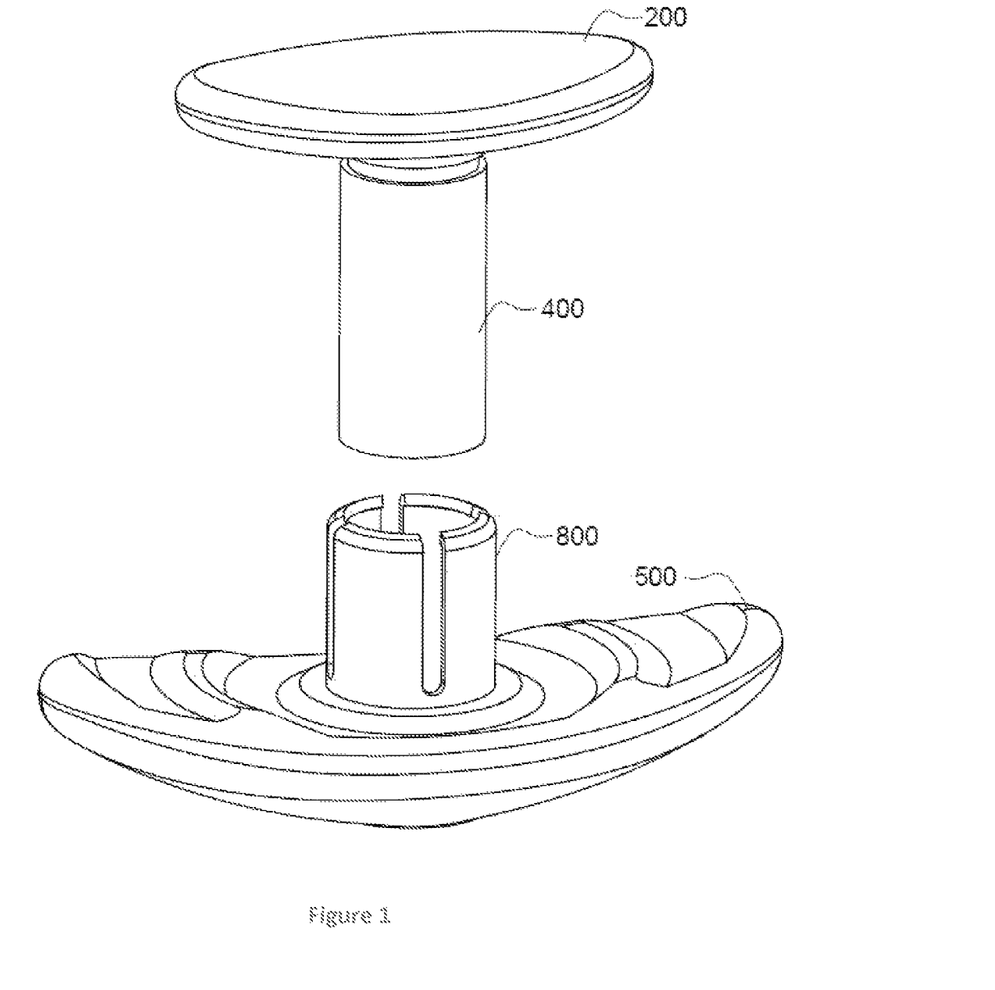
FIG. 1 shows an embodiment of the invention.

FIG. 1 shows one embodiment of the apparatus, consisting of an Inner Button 200, a Cylindrical Segment 400, an Outer Button 500, and a Spring Retainment Feature 800. In one or more embodiments, an assembly of the Outer Button 500 and Spring Retainment Feature 800 slides over an assembly of the Cylindrical Segment 400 and the Inner Button 200, enabling the device to both compress and lift the tissue around the wound, holding it in place for a period of time to heal as the apparatus materials degrade and are harmlessly absorbed into the patient.

Figure 2:
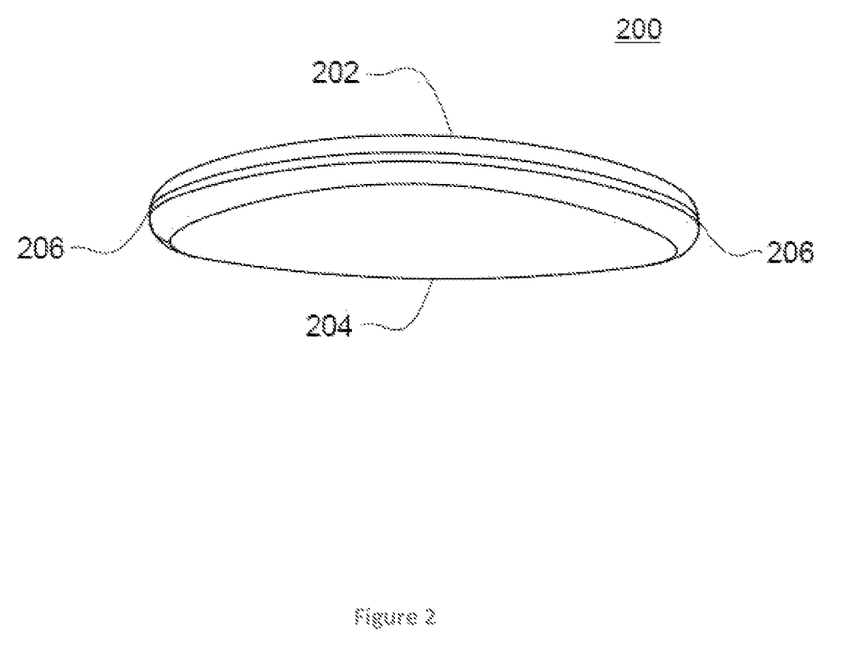
FIG. 2 shows a view of an embodiment of the inner button showing the surfaces of the inner button.

One or more embodiments of the Inner Button 200 is shown in FIG. 2. In one or more embodiments, the Inner Button 200 has a spherical convex contacting surface 202; this surface faces toward the wound tissue when the device is implanted. In one or more embodiments, the convex contacting surface 202 is made to enable the tissue to be furthest away from the wound at its center relative to its edges, distorting it.

The contacting surface of the Inner Button 202 is used to compress the wound tissue to keep it in place by pushing it outward. Too large a radius of curvature and the effect of pulling in the tissue is lessened. Too small of a radius of curvature and the tissue is compressed too much and potentially injured. The inventor found that somewhere around a 1.5" radius of curvature produces a good balance between these extremes.

In one or more embodiments, the shape of the Inner Button 200 is elliptical, characterized by a shorter and longer diameter. In one or more embodiments, the shape is circular, where the diameters are equal.

Figure 3:
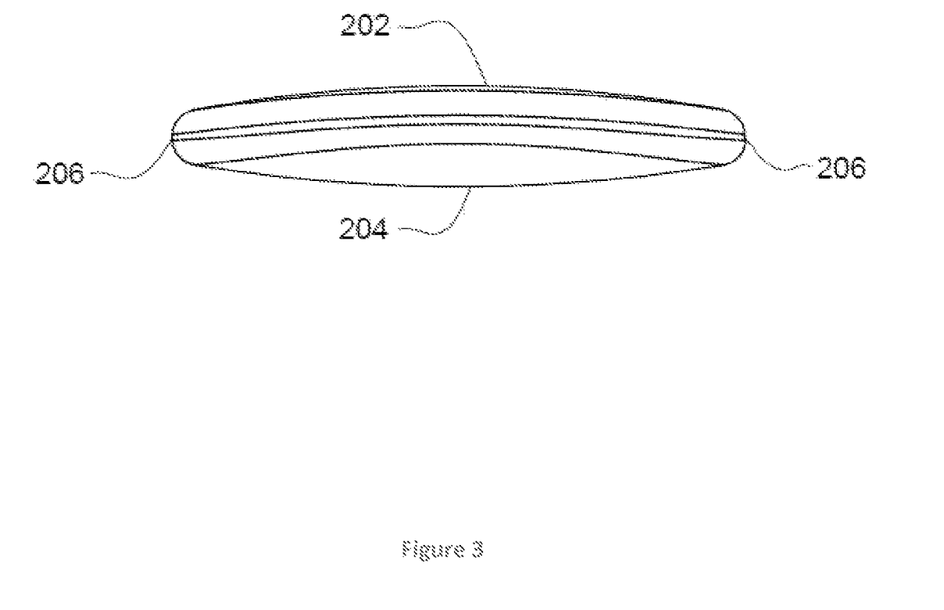
FIG. 3 shows a side view of an embodiment of the inner button.

FIG. 3 shows a side view of the Inner Button 200. The contacting surface of the Inner Button 202 is shown to be convex. In one or more embodiments, the back surface of the Inner Button 204 has a convex radius of curvature. The curvature encourages the Inner Button 200 to slide through the wound.

Figure 4:
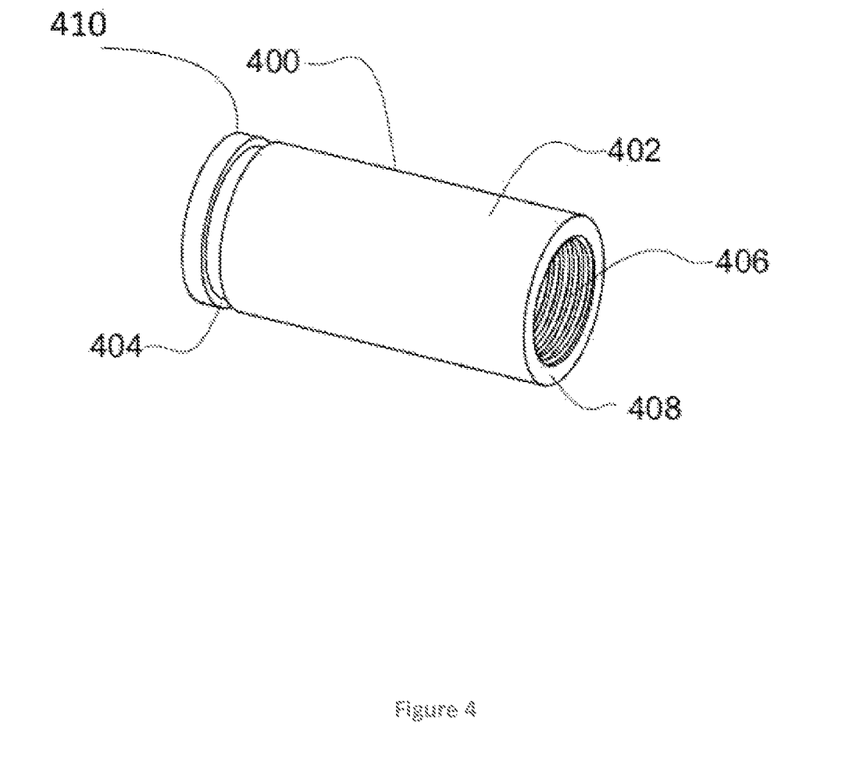
FIG. 4 shows an embodiment of the cylindrical segment.

One of more embodiments of the Cylindrical Segment 400 is shown in FIG. 4. In one or more embodiments, the contacting end of the Cylindrical Segment 410 is attached to the Inner Button 200 at the center of its contacting surface 202. In one or more embodiments, the Cylindrical Segment has a threaded hole 406 at its opposing end 408. In one or more embodiments, the threads of the Cylindrical Segment 406 are of sufficient length to enable an insertion tool to detachably attach to the Cylindrical Segment but easily detach once the device is inserted and compressed. In one or more embodiments, the Cylindrical Segment has a detent groove 404 along its outer surface near its contacting end. In one or more embodiments, the threaded hole of the cylindrical segment 406 is available to an instrument used to insert the apparatus into the wound. An insertion tool would keep the Inner Button 200 steady while moving the Outer Button 500 toward the Inner Button 200, compressing the tissue between it.

Figure 5:
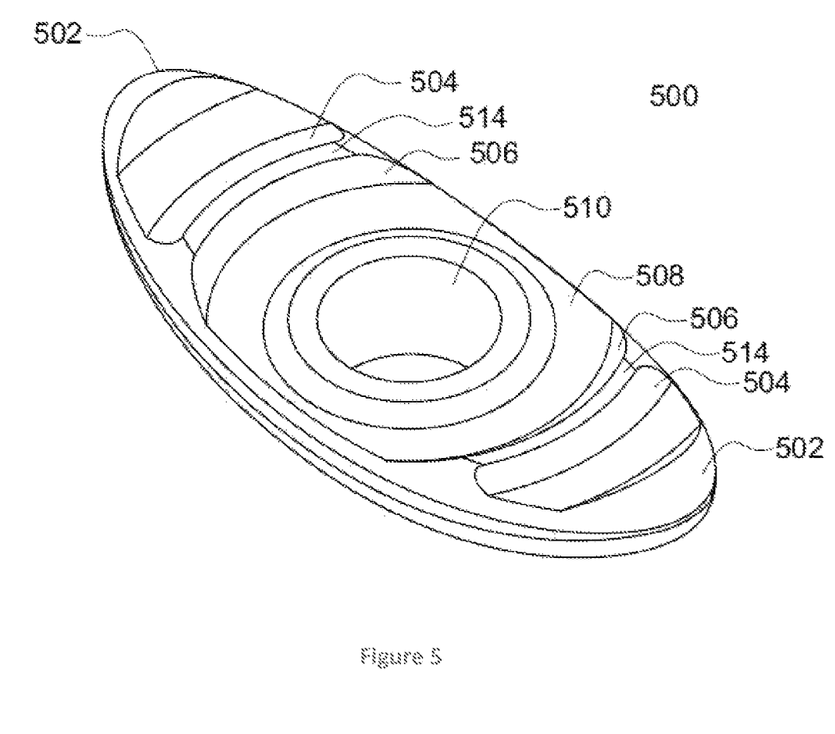
FIG. 5 shows a view of an embodiment of the outer button from the contacting surface.

One or more embodiments of the Outer Button 500 is shown in FIG. 5. In one or more embodiments, the shape of the Outer Button 500 is elliptical, characterized by a shorter and longer diameter. In one or more embodiments, the shape is circular, where the diameters are equal.

In one or more embodiments, the contacting surface of the Outer Button 502 is a spherically concaved surface; that is, it is made to enable the tissue to be furthest away from the wound at its center relative to its edges. In that way, the buttons compress the wound tissue to hold it in place. In one or more embodiments, the contacting surface of the Outer Button has a radial ridge 506 radially located from the center of the Outer Button along the longer diameter 502. The ridge is created by a raised section 514 between the end of the contacting surface 502 and the raised central portion of the contacting surface 508. The width of the ridge 506 is sufficient so that the tissue can be urged into it under compression, further keeping the apparatus from slipping.

In one or more embodiments, the longer diameter of the Outer Button 500 is short enough to enable the surgeon to insert the assembled device with the buttons roughly parallel to the wound surface, without having to force it through the laparoscopic tunnel. For most a 5 mm size would be sufficient. However, the device could be constructed in multiple sizes to accommodate larger or smaller tunnel sizes.

Figure 10:
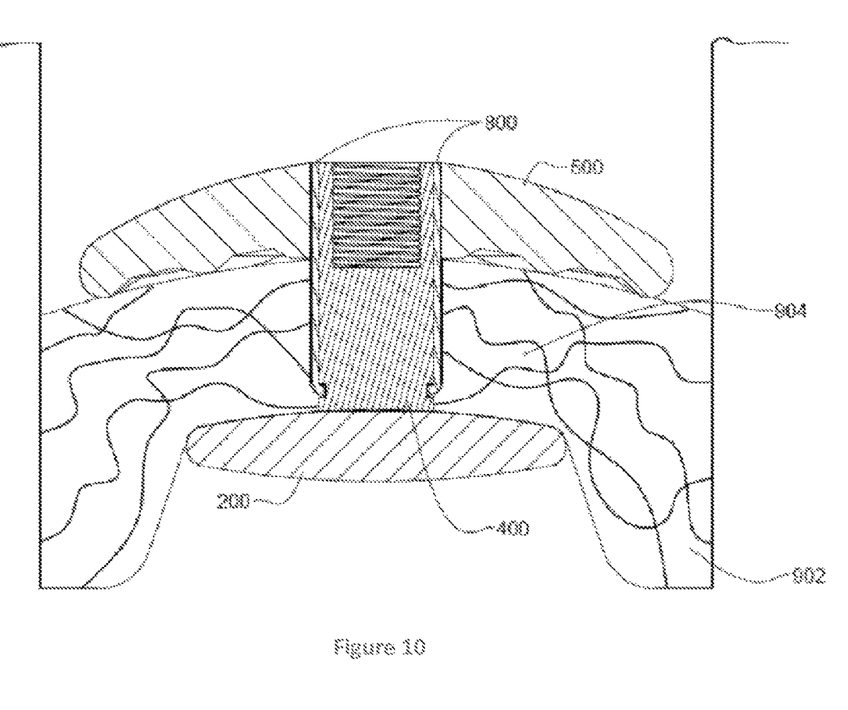
FIG. 10 shows a cutaway view of an embodiment of the implanted apparatus, showing how the apparatus bends and compresses the tissues between the convex contacting surface of the inner button and concave contacting surface of the outer button, thus reducing tissue slippage one might see when simply compressing the tissue.

In one or more embodiment the far contacting edges of the contacting surface of the Inner Button 206 are aligned with the center of the radial ridge of the contacting surface of the Outer Button 506 when the centers of the buttons are aligned. In this way, the contacting edges of the Inner Button 206 will urge the tissue into the radial ridge of the Outer Button 506, as shown in FIG. 10.

Figure 6:
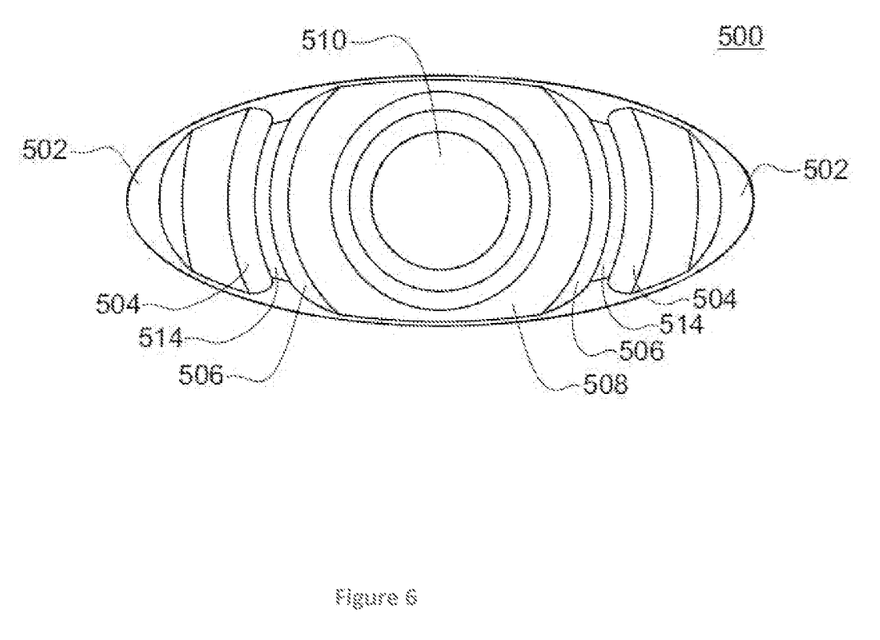
FIG. 6 shows another view of an embodiment of the outer button from the contacting surface.

FIG. 6 shows a top down view of one or more embodiments of the contacting surface of the Outer Button, showing a clearer view of the ridges 506.

Figure 7:
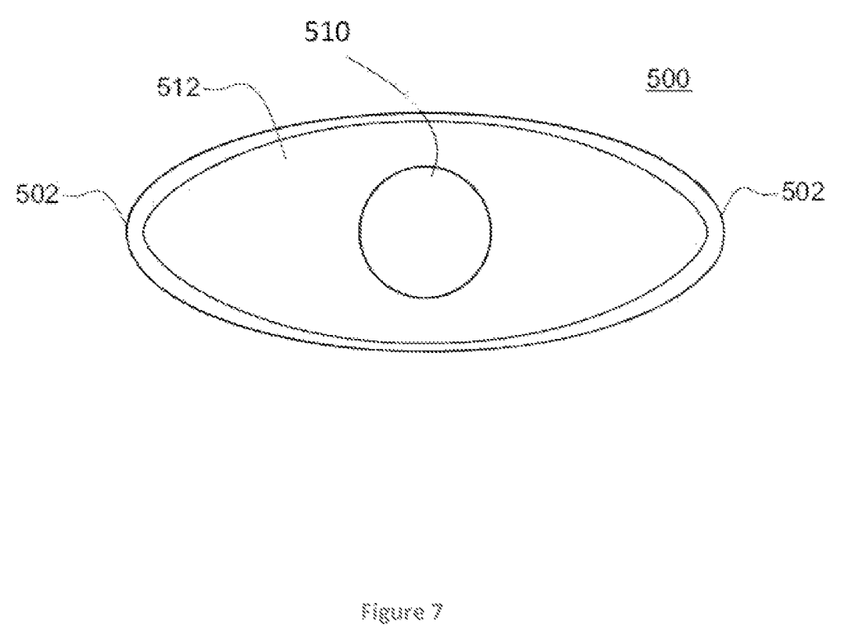
FIG. 7 shows an embodiment of the outer button from the connection side.

FIG. 7 shows the back surface of one or more embodiments of the Outer Button 512, which is featureless except for the hole through the center 510.

Figure 8:
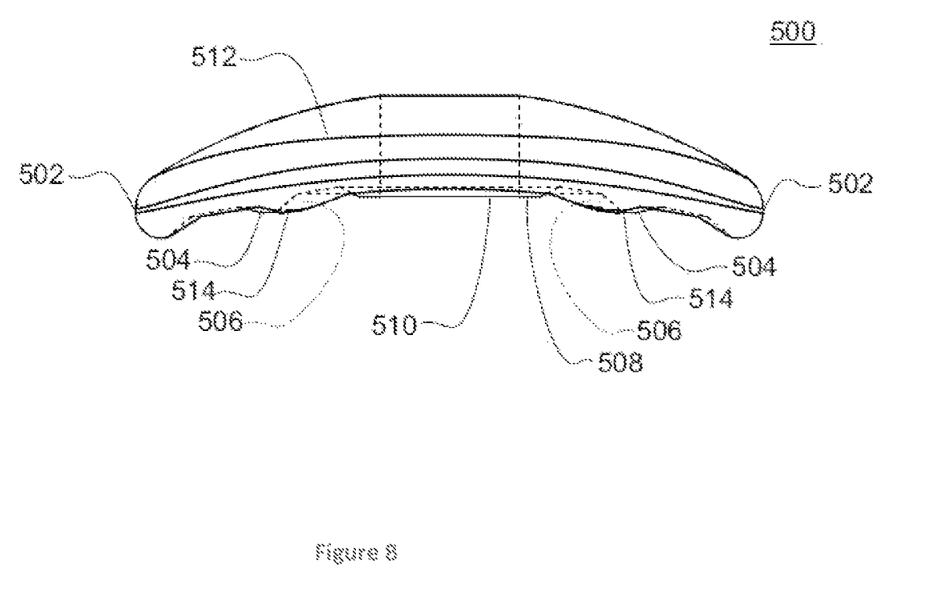
FIG. 8 shows a side view of an embodiment of the outer button.

FIG. 8 show a side view of one or more embodiments of the Outer Button.

Figure 9:
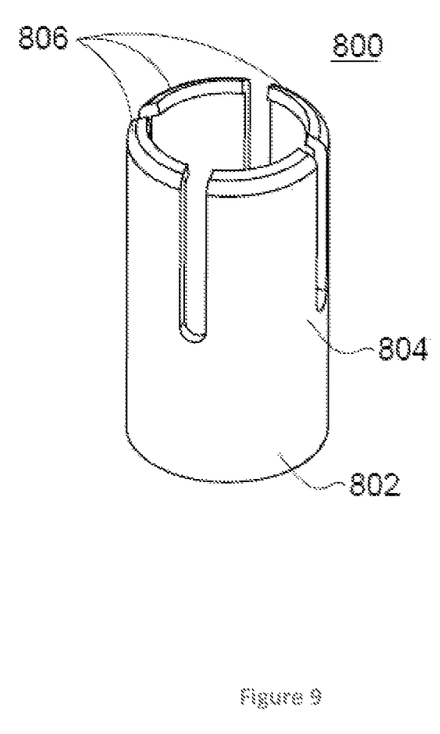
FIG. 9 shows a view of an embodiment of the spring retainment feature.

One or more embodiments of the Spring Retainment Feature are shown in FIG. 9. The Spring Retainment Feature 800 consists of a set of strips 804 arranged radially about a cylindrical base 802. The Spring Retainment Feature is attachable to the center of the Contacting Surface of the Outer Button 508 at the cylindrical base 802.

In one or more embodiments, the cylindrical base is not needed as the Spring Retainment Feature is attached to the center of the contacting surface 508 with only the set of strips 804. The ends of the curved strips 806 are bent radially inwards, such that they are able to fit into the detent groove 404 without slipping over the surface of the cylindrical segment 402.

In other embodiments, the Spring Retainment Feature is attached to a well in the center region of the contacting surface 508, so that the length of the strips is longer and they flex easier. In other embodiments, the cylindrical base is not necessary as the strips are attached directly to the contacting surface 508.

In one or more embodiments, the radial ridge of the Outer Button 506 is far enough away from the center so that there is a region around the center 508 large enough to allow the placement of the Spring Retainment Feature 800 without interfering with the radial ridge 506.

In one or more embodiments, the device would be built as two subassemblies. The first subassembly would consist of the Inner Button 200 and the Cylindrical Segment 400. The Inner Button 200 would be permanently attached to the cylindrical segment 400, such that the threaded end of the cylindrical segment would be open. The outer button 500 would be permanently attached to the Spring Retainment Feature 800, such that the bent ends of the Spring Retainment Feature 806 would slide over the outer surface of Cylindrical Segment 402 and into the detent groove 404.

In one or more embodiments, the method of implanting the device would require that the second subassembly be slid over the first subassembly, such that the bent ends of the Spring Retainment Feature 806 are fitted over the outer wall of the cylindrical segment 402 far enough so that it stays together, but not so far that the bent ends 806 are in the detent groove 404. An insertion tool could screw into the threads of the Cylindrical Segment 408 and enable the surgeon to push the Inner Button 200 through the wound. The insertion tool would then exert a force on the back surface of Outer Button 512, pushing the second subassembly toward the first assembly while the first subassembly is held in place by its attachment to the insertion tool. From the force, the Outer Button 500 would slide toward the Inner Button 200 until the bent ends of the Spring Retainment Feature 806 move into the detent groove 404. The surgeon would feel the "click" as the bent ends 806 slide into the groove 404.

In one or more embodiments, the device would appear in cross section as shown in FIG. 10. The curvature of the Inner button 200 would compress the tissue surrounding the wound 902 into the gap between the Inner Button 200 and Outer Button 500, also pushing it slightly upward 904. The two motions of compression and bending would act to keep the tissue in place. The Inner Button ends 206 would urge the tissue into the grooves in the contacting surface of the Outer Button 506, further keeping the tissue in place.

General Composition of the Wound Closure Device

Materials specified for the device are specific for its intended application and use. The scope of materials that will satisfy the requirements of this application is unusually narrow. This is a direct consequence of the specificity and functional demands characteristic of the intended surgical application.

The intention for the device is to close and secure the trocar port defect in the fascia. This requires a known and finite healing interval of some three to five months. Its purpose fulfilled at the end of this period, making continued presence of the closure device a potential liability. To prevent it from becoming a source for irritation once the healing process is completed, an implanted closure device should be removed. Consequently, to avoid the need for a second surgical intervention to remove the device, Maurus and Kaeding (Maurus, P. B. and Kaeding, C. C., "Bioabsorbable Implant Material Review", Oper. Tech. Sports Med 12, 158-160, 2004) found it was a primary requirement for the wound closure device is that it is biodegradable. This means that the materials will degrade or disintegrate, being absorbed in the surrounding tissue in the environment of the human body, after a definite, predictable and desired period of time. One advantage of such materials over non-degradable or essentially stable materials is that after the interval for which they are applied (i.e. healing time) has elapsed, they are no longer a contributing asset and do not need subsequent surgical intervention for removal, as would be required for materials more stable and permanent. This is most significant as it minimizes risks associated with repeat surgeries and the additional trauma associated with these procedures.

A disadvantage of these types of materials is that their biodegradable characteristic makes them susceptible to degradation under normal ambient conditions. There is usually sufficient moisture or humidity in the atmosphere to initiate their degradation even upon relatively brief exposure. This means that precautions must be taken throughout their processing and fabrication into useful forms, and in their storage and handling, to avoid moisture absorption. This is not a serious limitation as many materials require handling in controlled atmosphere chambers and sealed packaging; but it is essential that such precautions are observed. Middleton and Tipton (Middleton, J. and Tipton A. "Synthetic Biodegradable Polymers As Medical Devices" Medical Plastics and Biomaterials Magazine, March 1998) found that this characteristic also dictates that their sterilization before surgical use cannot be done using autoclaves, but alternative approaches must be employed (e.g. exposure to atmospheres of ethylene oxide or gamma radiation with cobalt 60).

While biodegradability is an essential material characteristic for the wound closure device, the intended application is such that a further requirement is that the material is formulated and manufactured with sufficient compositional and process control to provide a precisely predictable and reliable degree of biodegradability. This means a typical biodegradation interval of three to five months, corresponding to the healing interval for the trocar defect in the fascia layer.

In these materials, simple chemical hydrolysis of the hydrolytically unstable backbone of the polymer is the prevailing mechanism for its degradation. As discussed in Middleton and Tipton (Middleton, J. and Tipton A referenced previously), this type of degradation when the rate at which water penetrates the material exceeds that at which the polymer is converted into water-soluble materials is known as bulk erosion.

Biodegradable polymers may be either natural or synthetic. In general, synthetic polymers offer more advantages than natural materials in that their compositions can be more readily finely-tuned to provide a wider range of properties and better lot-to-lot uniformity and, accordingly, offer more general reliability and predictability and are the preferred source.

Synthetic absorbable materials have been fabricated primarily from three polymers: polyglycolic acid (PGA), polylactic acid (PLA) and polydioxanone (PDS). These are alpha polyesters or poly (alpha-hydroxy) acids. The dominant ones are PLA and PGA and have been studied for several decades. Gilding and Reed (Gilding, D. K and Reed A. M., "Biodegradable Polymers for Use in Surgery" Polymer 20, 1459-1464) discussed how each of these materials has distinctive, unique properties. One of the key advantages of these polymers is that they facilitate the growth of blood vessels and cells in the polymer matrix as it degrades, so that the polymer is slowly replaced by living tissue as the polymer degrades ("Plastic That Comes Alive: Biodegradable plastic scaffolds support living cells in three dimensional matrices so they can grow together into tissues and even whole organs" by Cat Faber Strange Horizons http://www.strangehorizons.com/2001/20010305/plastic.shtml)

In recent years, researchers have found it desirable for obtaining specific desirable properties to prepare blends of these two dominant types, resulting in a highly useful form, or co-polymer, designated as PLGA or poly (lactic-co-glycolic acid). Asete and Sabilov (Asete, C. E. and Sabilov C. M., "Synthesis and Characterization of PLGA Nanoparticles", Journal of Biomaterials Science—Polymer Edition 17(3) 247-289 (2006)) discuss how this form is currently used in a host of FDA-approved therapeutic devices owing to its biodegradability and biocompatibility.

In one or more embodiments, the biodegradable wound closure device may be made of biodegradable material of different stability (i.e. half-life). Since the material that is in the device is in direct contact with the fascia or lending support to that needs to stay in place for a few months. In one or more embodiments, the Cylindrical Segment 400 and Spring Retainment Feature 800 would degrade sooner than the Inner Button 200 and Outer Button 500, so that the ends of the defect are allowed to grow together while protecting the surface of the defect.

Material for the Outer Button

Depending upon the ratio of lactide-to-glycolide used for polymerization, different forms or grades of PLGA are obtainable. These are usually identified according to the monomers' ratio and are so designated in the literature and suppliers' brochures. PLGA has been successful as a biodegradable polymer for medical applications because it undergoes hydrolysis in the body to produce the original monomers, lactic acid and glycolic acid.

The two monomers associated with PLGA, lactide and glycolide, under normal physiological conditions, are byproducts of various metabolic pathways in the human body. Since the body effectively deals with these two monomers, there is minimal system toxicity associated with use of this co-polymer. A notable feature of PLGA is that it is possible to tailor the polymer degradation interval by adjusting the ratio of monomers. In light of the versatility of the PLGA co-polymer and its record of successful use in a wide range of bio-absorbable applications, it is the specified material for the Outer Button 500.

What is claimed is:

1. An implantable biodegradable device to promote the healing of a laparoscopic wound, the device comprising:

an inner button having a spherical convex contacting surface and a back surface, the contacting surface having a first longer diameter and a first shorter diameter whereby the first longer diameter is sufficiently smaller than the wound opening to enable one to insert it with the contacting surface perpendicular to the opening, and sufficiently large enough to cover a sufficient amount of the wound to promote healing;

a cylindrical segment with an outer surface, an inner surface, a contacting end and an opposing end, the outer surface having a radial detent groove on the contacting end and the inner surface having inner threads on the opposing end, the cylindrical segment attachable to the center of the contacting surface of the inner button at the contacting end; and an outer button, having a second longer diameter, second shorter diameter, a spherically convex contacting surface and a back surface, the outer button having a hole through its center to allow the cylindrical segment to pass through the hole, the second longer diameter at least as long as the first longer diameter but sufficiently smaller than the wound opening to enable one to insert it with the contacting surface perpendicular to the opening;

a spring retainment feature, consisting of a plurality of strips arranged in a radial fashion, the spring retainment feature attachable to the center of the contacting surface of the outer button at the base of the strips, the strips having ends bent radially inward, the spring retainment feature having sufficient radius that it slides over the cylindrical segment, the ends of the strips bent such that they can contact the detent groove and will resist movement.

2. The device in claim 1, wherein the contacting surfaces of the outer button and inner button have a spherical radius of about 1.5 inches.

3. The device in claim 1, wherein the contacting surface of the outer button further comprises a raised area at the center, raised areas at the ends of the second longer diameter and radial ridges between them wherein they form indentations between the radial ridge and the raised area at the end such that the distance between the centers of the indentations is about equal to the first longer radius of the first longer diameter of the inner button, and the indentations are sufficiently deep and wide enough to enable the tissue to enter the indentation.

4. The device in claim 3, wherein the indentations are about 2 mm deep.

5. The device in claim 1, wherein the detent groove of the cylindrical segment is placed so that when the bent ends of the spring retainment feature engage the detent groove, the top of the cylindrical segment is roughly adjacent to the back surface of the outer button.

6. The device in claim 1, wherein the spring retainment feature has a base, such that the strips do not directly attach to the contacting surface of the outer button.

7. The device in claim 1, wherein the spring retainment feature is permanently attached to the outer button and the cylindrical segment is permanently attached to the inner button.

8. The device in claim 1, wherein the outer button has a depression in the surface around the central hole, so that the distance between the base of the strips and the bent ends can be longer while still contacting the detent groove.

9. The device in claim 1, wherein the outer button is made of PLGA.

10. The device in claim 1, wherein the components of the device are made from biodegradable polymers of differing degradation rates so that the cylindrical segment and spring retainment feature degrade faster than the inner button and outer button.

11. A method for implanting the device in claim 1, the method comprising:

attaching the inner button to the cylindrical segment to create a first subassembly;

attaching the outer button to the spring retainment feature to create a second subassembly;

sliding the spring retainment feature over the cylindrical segment so that the spring retainment feature overlaps the cylindrical segment sufficiently so that they stay together, but the contacting surfaces of the inner and outer button are far enough apart that they will compress the tissue around the wound, holding the tissue in place, but no so compressed as to injure the tissue;

connecting an insertion tool to the threads of the cylindrical segment;

pushing the inner button through the wound;

pushing on the back surface of the outer button while holding the inner button steady, which slides the spring retainment feature over the cylindrical segment until the bent ends of the spring retainment feature engage the detent groove;

detaching the insertion tool from the threads of the cylindrical segment;

the device remaining in a non-degraded state long enough to enable the wound to form a structural matrix.

12. The device in claim 1, wherein the back surface of the inner button is sufficiently convex to enable the inner button to slide through the wound.

\* \* \* \* \*